United States Patent
Shao et al.

(10) Patent No.: US 10,568,877 B2
(45) Date of Patent: *Feb. 25, 2020

(54) PREPARATION AND ANTI-HSV-1 APPLICATION OF QUINOLINONE DERIVATIVES

(71) Applicant: OCEAN UNIVERSITY OF CHINA, Qingdao (CN)

(72) Inventors: Changlun Shao, Qingdao (CN); Changyun Wang, Qingdao (CN); Rufang Xu, Qingdao (CN); Feifei Guan, Qingdao (CN); Meiyan Wei, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,050

(22) Filed: Oct. 2, 2017

(65) Prior Publication Data
US 2018/0028524 A1 Feb. 1, 2018

Related U.S. Application Data

(63) Continuation-in-part of application No. PCT/CN2016/077663, filed on Mar. 29, 2016.

(30) Foreign Application Priority Data

Sep. 6, 2015 (CN) .......................... 2015 1 0559006

(51) Int. Cl.
*A61K 31/4709* (2006.01)
*A61K 31/4704* (2006.01)

(52) U.S. Cl.
CPC ...... *A61K 31/4704* (2013.01); *A61K 31/4709* (2013.01)

(58) Field of Classification Search
CPC .................................................. A61K 31/4709
See application file for complete search history.

(56) References Cited

U.S. PATENT DOCUMENTS

2012/0040033 A1* 2/2012 Armstrong ........... A61K 36/185
424/769

OTHER PUBLICATIONS

An et al (J. Nat. Prod. 2013, 76:1896-1901) (Year: 2013).*
Ren et al (Virol Sin, 2010; 25(2):107-14). (Year: 2010).*

* cited by examiner

*Primary Examiner* — Marcos L Sznaidman
*Assistant Examiner* — Rayna Rodriguez

(57) ABSTRACT

Provided herein are quinolinone derivatives and their uses as antiviral drugs, for example, for treatment of HSV-1 infection. Also provided herein are pharmaceutically acceptable compositions comprising the quinolinone derivatives and the uses of the composition in the treatment of diseases caused by HSV-1 virus.

2 Claims, No Drawings

PREPARATION AND ANTI-HSV-1 APPLICATION OF QUINOLINONE DERIVATIVES

CROSS-REFERENCE TO RELATED APPLICATIONS

This is a continuation-in-part application of the International Patent Application No. PCT/CN/2016/077663, filed Mar. 29, 2016, which claims priority to Chinese Patent Application No. 201510559006.7, filed Sep. 6, 2015, both of which are incorporated herein by reference in their entirety.

FIELD OF INVENTION

The present invention relates generally to the field of anti-viral agents. In one embodiment, provided herein are quinolinone derivatives, their combinations, their methods of preparation and their uses as anti-viral agents, for example, for treatment of disease caused by HSV-1 virus.

BACKGROUND OF THE INVENTION

Herpes Simplex Virus 1 (HSV-1) is an enveloped DNA virus, with high incidence, long latency, perineural, and incubating in peripheral nervous system. Young children, organ transplant recipients or people with diminished immunity are susceptible to infection of HSV-1 virus. Once infected, HSV-1 virus can cause serious encephalitis, keratitis and even death. Nucleoside antiviral medications, such as acyclovir, famciclovir, and valacyclovir, are the most effective medications available for people infected with HSV. These medications can help to reduce the severity and frequency of symptoms, but cannot cure the infection. In view of the increasing cases of drug-resistant pathogens, it is imperative to develop new and effective antiviral drugs. Marine microorganisms are widely recognized as prolific sources of biologically active and structurally unique natural products because of their unique living condition such as high salinity, high pressure, low temperature, oxygen deficiency and darkness. However, there are few reports of marine-derived antiviral entity. (Newman, D. J.; Cragg, G. M. *J. Nat. Prod.* (2012) 75:311-335; Blunt, J. W.; Copp, B. R.; Keyzers, R. A.; Munro, M. H. G.; Prinsep, M. R. *Nat. Prod. Rep.* (2014) 31:160-258, and previous annual reports). Thus, there is a need of developing new and effective antiviral drugs.

SUMMARY OF THE INVENTION

The present invention provides quinolinone derivatives or pharmaceutical compositions thereof with antiviral activity. In one embodiment, these derivatives or pharmaceutical compositions thereof have anti-HSV-1 activity, thus can be used as antiviral agents in treatment of diseases caused by HSV-1. In one embodiment, provided herein are compounds having the Formula (I):

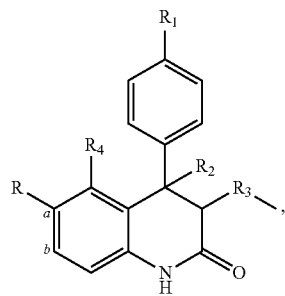

or a pharmaceutically acceptable salt thereof, wherein R is H.

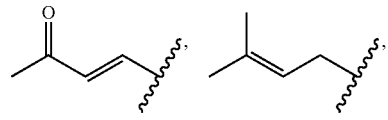

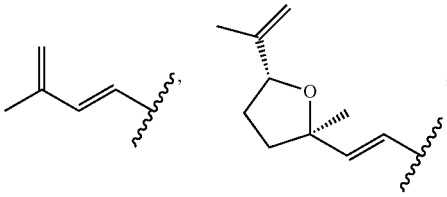

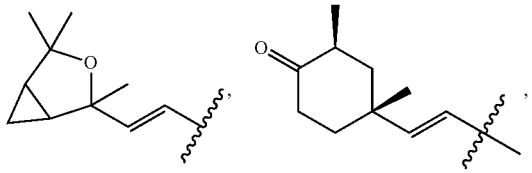

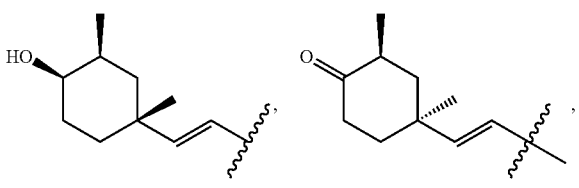

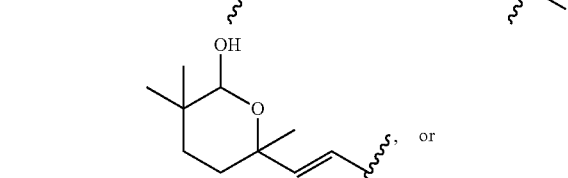

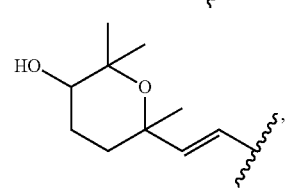

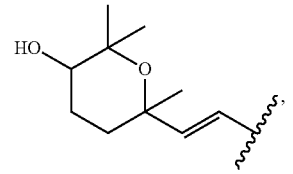

or R is formed together with the carbon atoms a and b of the phenyl group to which they are attached in the following substituent

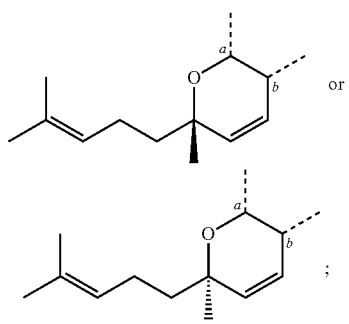

$R_1$ is H or $OCH_3$; $R_2$ is H, OH, or $OCH_3$; $R_3$ is H, OH, or $OCH_3$; and $R_4$ is H or OH.

In another embodiment, there are provided compounds having the Formula (II):

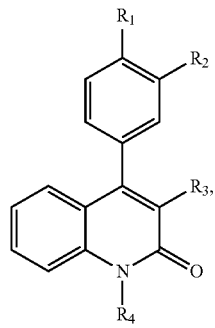

II or a pharmaceutically acceptable salt thereof, wherein $R_1$ is H or $OCH_3$; $R_2$ is H or OH; $R_3$ is OH or $OCH_3$; and $R_4$ is H or $CH_3$.

DETAILED DESCRIPTION OF THE INVENTION

In one embodiment, compounds having the Formula (I) can be one of the following:

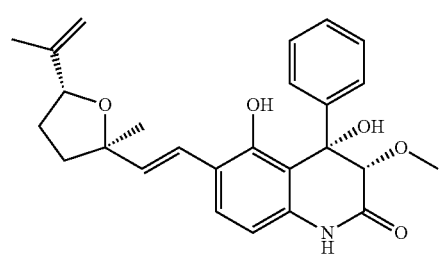

1

2a

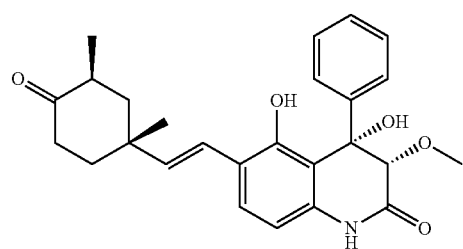

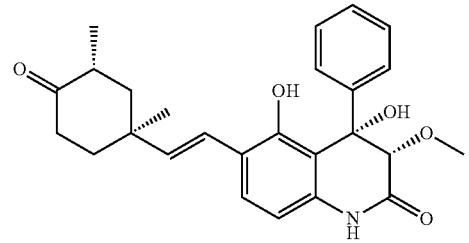

2b

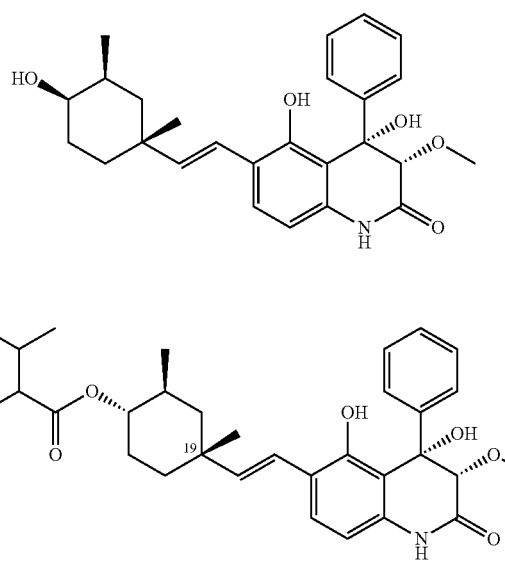

3

3a 19R
3b 19S

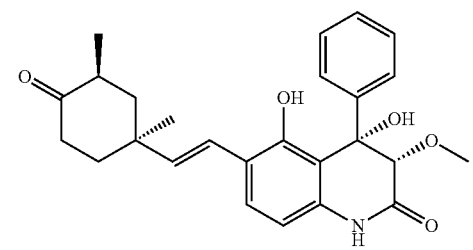

4

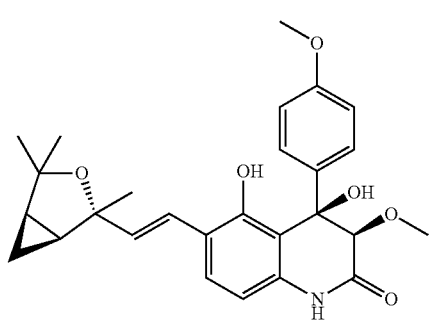

5

6
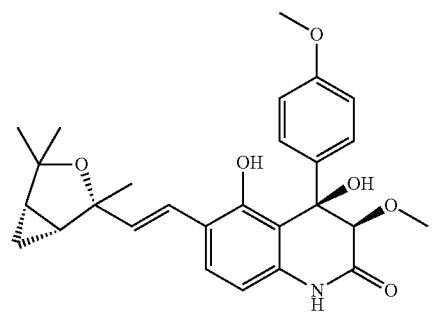
7
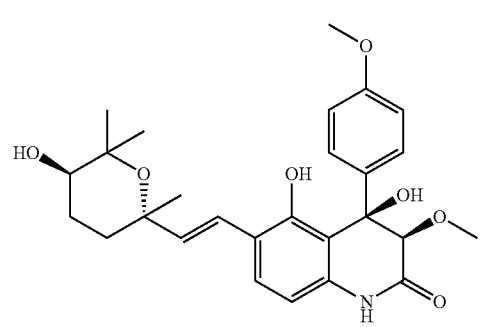
8
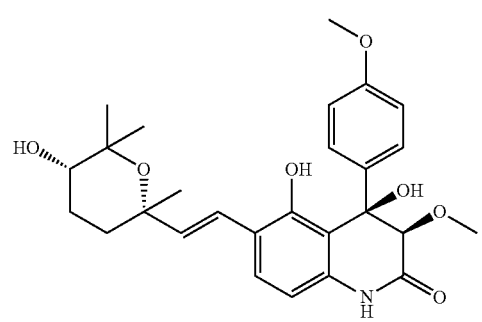
9
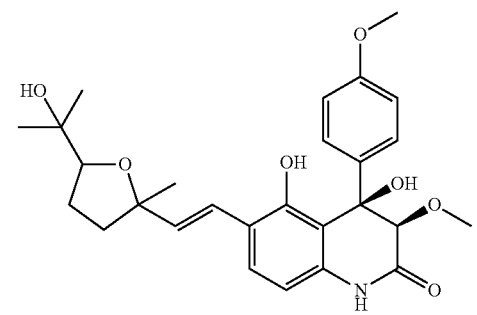
10
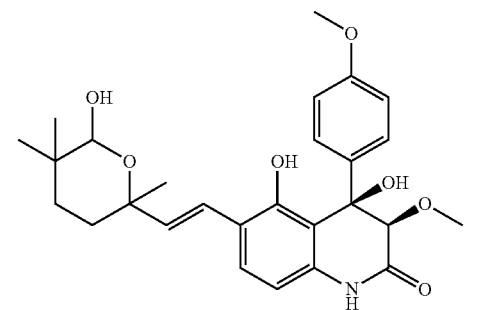
11
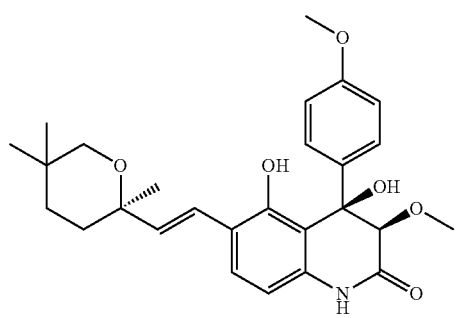
12
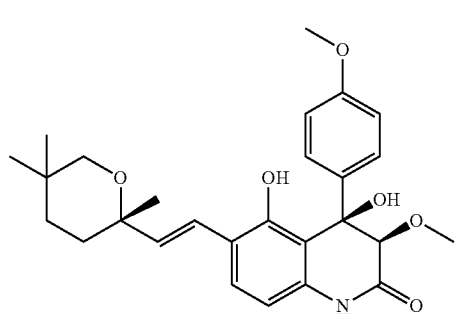
13
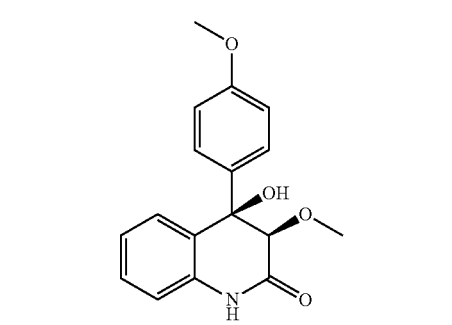
14
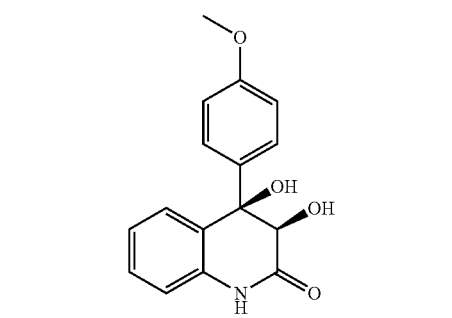
15
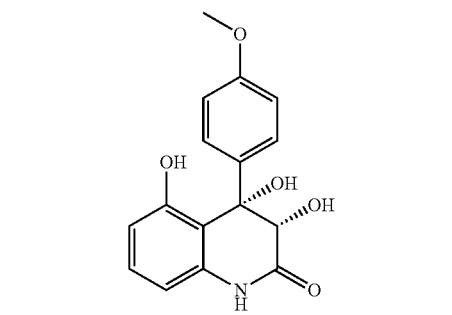

16
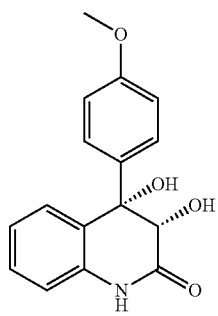
17
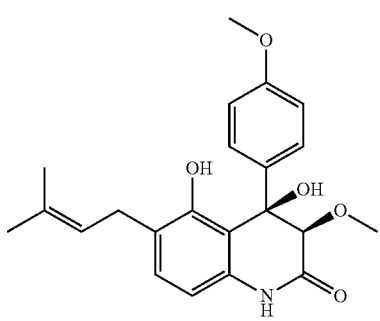
18
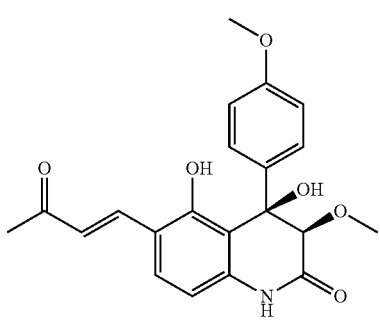
19
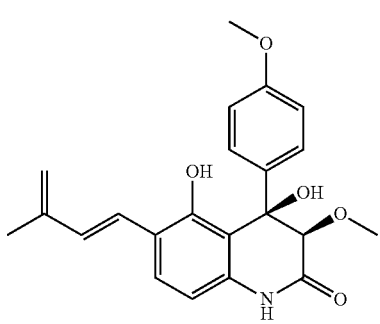
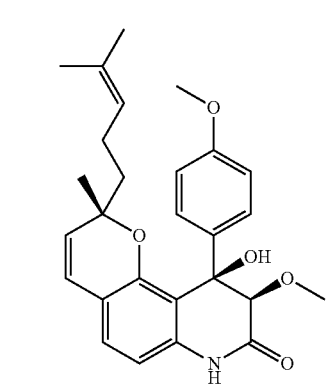
21
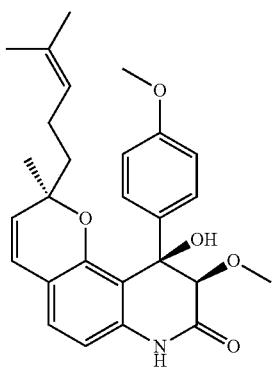
In one embodiment, compounds having the Formula (II) can be one of the following:
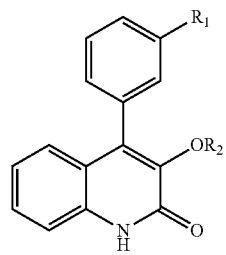
22 R1 = OH, R2 = Me
23 R1 = H, R2 = Me
24 R1 = H, R2 = H
25
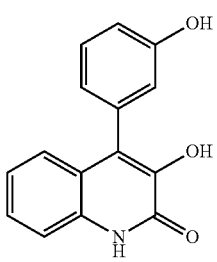
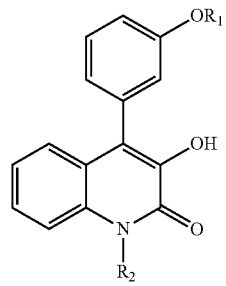
26 R1 = Me, R2 = Me
27 R1 = Me, R2 = H
28 R1 = H, R2 = Me -continued

29

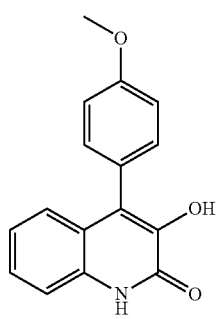

30

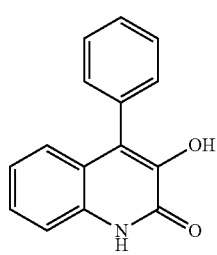

Compounds 1-4 can be found in documents [1]-[3]. Compounds 5-8 were reported in document [4]. Compounds 9, 10, 18-21 were reported in documents [5]-[6]. Compounds 11 and 12 can be found in documents [7]-[8]. Compounds 13 and 14 were reported in document [9]. Compounds 15 and 16 can be found in literature [10]. Compound 17 can be found in document [11]. Compounds 22-28 were reported in document [12]. Compounds 29 and 30 were reported in documents [13]-[14].

Quinolinone derivatives provided herein include stereoisomers, geometric isomers, tautomers or the combination thereof.

The term "pharmaceutically acceptable salt" refers to organic or inorganic salts of a compound disclosed herein. Pharmaceutically acceptable salts are well known in the art. For example, details of pharmaceutically acceptable salts were described in "Salt selection for basic drugs", Int. J. Pharm. (1986), 33, 201-217, which is incorporated herein by reference.

The quinolinone derivatives provided herein are products isolated from marine fungus. These compounds showed potent antiviral activity against HSV-1, with huge potential to be used as anti-HSV-1 agents.

Information on microbiological preservation: name of the preservation unit: The Chinese General Microbiological Culture Collection Center; address of the depository: China General Microbiological Culture Collection Center, Institute of Microbiology Chinese Academy of Sciences, NO.1 West Beichen Road, Chaoyang District, Beijing 100101, China; date of deposit: 17 Dec. 2012; preservation number: CGMCC 6959; classification terms: *Scopulariopsis* sp.

In one embodiment, the present invention provides uses of compounds having the Formula (I),

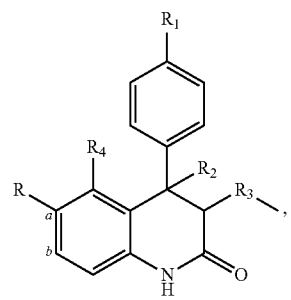

or a pharmaceutically acceptable salt thereof, in the preparation of medicament for treating diseases caused by HSV-1, wherein R is H,

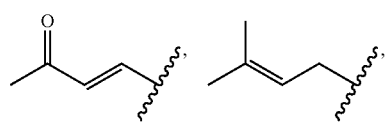

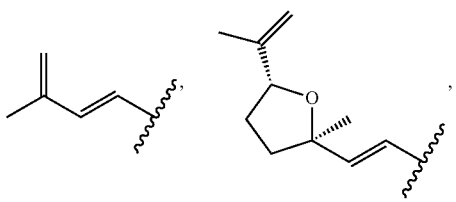

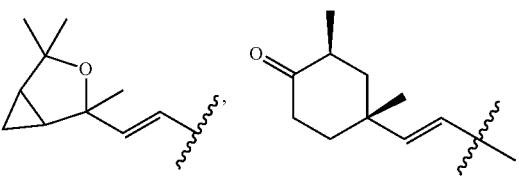

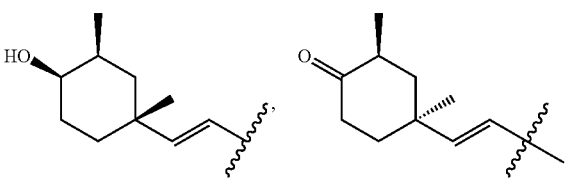

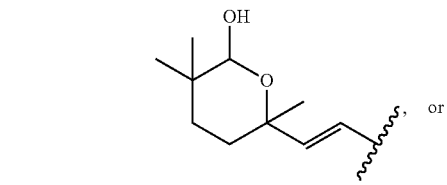

or

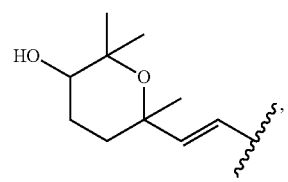

or R is formed together with the carbon atoms a and b of the phenyl group to which they are attached in the following substituent

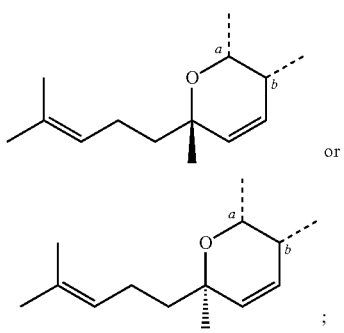

or

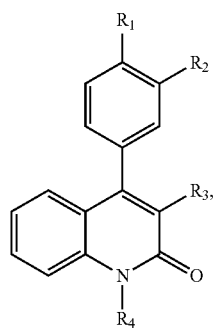

;

$R_1$ is H or $OCH_3$; $R_2$ is H, OH, or $OCH_3$; $R_3$ is H, OH, or $OCH_3$; and $R_4$ is H or OH. In one embodiment, compounds having the Formula (I) can be one of the compounds (1)-(21) disclosed herein.

In another embodiment, the present invention provides uses of compounds having the Formula (II),

II

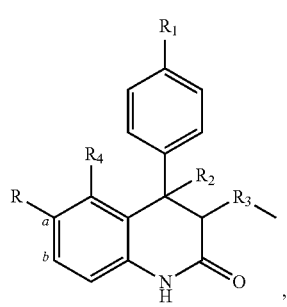

or a pharmaceutically acceptable salt thereof, in the preparation of medicament for treating diseases caused by HSV-1, wherein $R_1$ is H or $OCH_3$; $R_2$ is H or OH; $R_3$ is OH or $OCH_3$; and $R_4$ is H or $CH_3$. In one embodiment, compounds having the Formula (II) can be one of the compounds (22)-(30) disclosed herein.

The present invention also provides a method of treating a viral infection, comprising administering to a subject in need thereof an effective amount of a compound having
(i) the Formula (I),

I

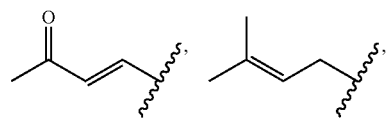

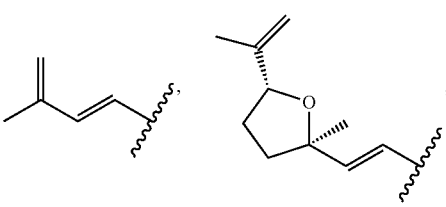

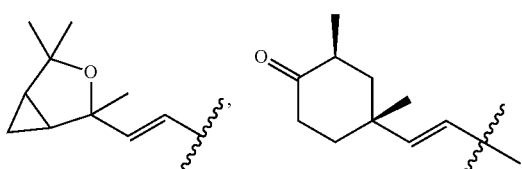

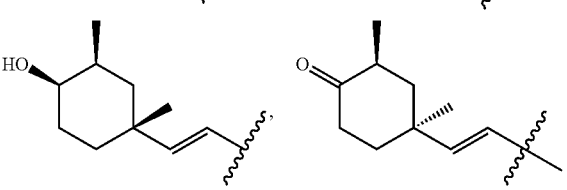

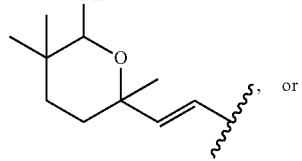

, or

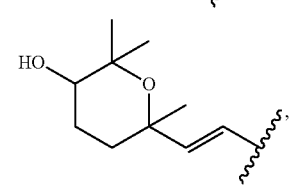

or R is formed together with the carbon atoms a and b of the phenyl group to which they are attached in the following substituent

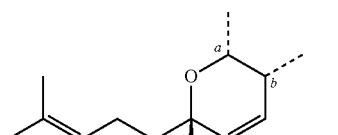

or

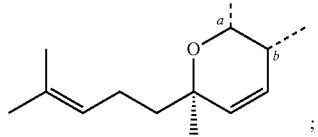

;

or a pharmaceutically acceptable salt thereof, wherein R is H, $R_1$ is H or $OCH_3$; $R_2$ is H, OH, or $OCH_3$; $R_3$ is H, OH, or $OCH_3$; and $R_4$ is H or OH; or (ii) the Formula (II),

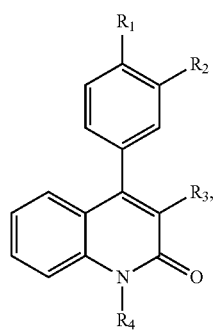

or a pharmaceutically acceptable salt thereof, wherein $R_1$ is H or $OCH_3$; $R_2$ is H or OH; $R_3$ is OH or $OCH_3$; and $R_4$ is H or $CH_3$.

In one embodiment, compound having the Formula (I) can be one of the compounds (1)-(21) disclosed herein. In one embodiment, compound having the Formula (II) can be one of the compounds (22)-(30) disclosed herein. In one embodiment, the compound can be one of compounds (1), (2), or (4) disclosed herein. In one embodiment, the viral infection is caused by herpes simplex virus 1 (HSV-1).

The term a "therapeutically effective amount", "effective amount" or a "sufficient amount" of a compound of the present application is a quantity sufficient to, when administered to the subject, including a mammal, for example a human, effect beneficial or desired results, including clinical results. An "effective amount" or synonym thereto thus depends upon the context in which it is being applied. In one embodiment, therapeutically effective amounts of the compounds of the present application are used to treat, modulate, attenuate, reverse, or effect diseases associated with HSV-1 infections in a mammal. Therefore an "effective amount" is intended to mean that amount of a compound that is sufficient to treat, prevent or inhibit HSV-1 infection or a disease associated with HSV-1 infection. The amount of a given compound of the present application that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. For example, a "therapeutically effective amount" of a compound of the present application is an amount which prevents, inhibits, suppresses or reduces HSV-1 infection (e.g., as determined by clinical symptoms or the amount of virus) in a subject as compared to a control. As defined herein, a therapeutically effective amount of a compound of the present application may be readily determined by one of ordinary skill by routine methods known in the art.

The present invention also provides a method of inhibiting activities of herpes simplex virus 1 (HSV-1), comprising the step of contacting a cell with a compound having (i) the Formula (I),

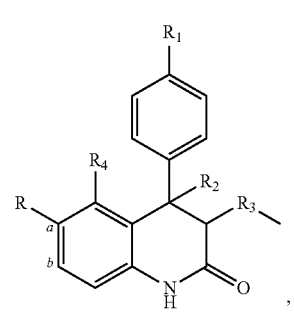

or a pharmaceutically acceptable salt thereof,
wherein R is H,

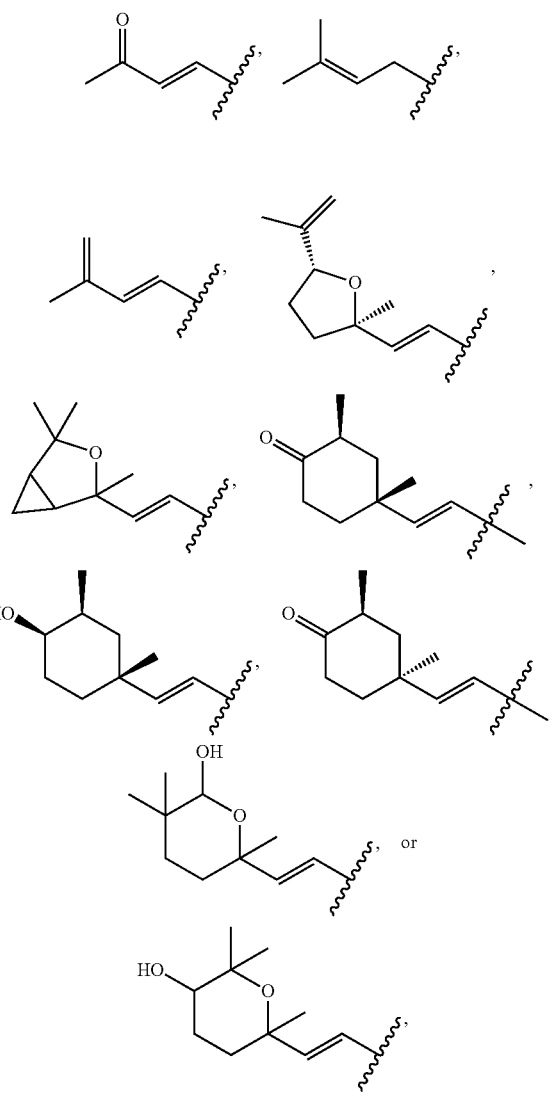

or R is formed together with the carbon atoms a and b of the phenyl group to which they are attached in the following substituent

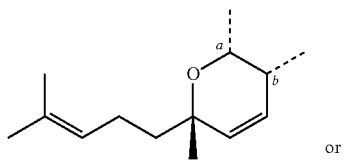

or

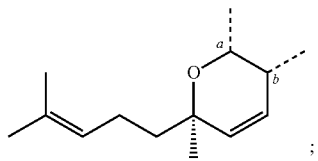

;

$R_1$ is H or OCH$_3$; $R_2$ is H, OH, or OCH$_3$; $R_3$ is H, OH, or OCH$_3$; and $R_4$ is H or OH; or (ii) the Formula (II),

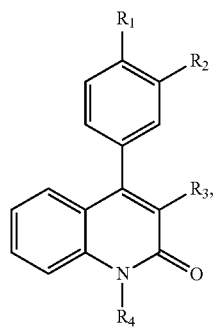

or a pharmaceutically acceptable salt thereof, wherein $R_1$ is H or OCH$_3$; $R_2$ is H or OH; $R_3$ is OH or OCH$_3$; and $R_4$ is H or CH$_3$.

In one embodiment, compound having the Formula (I) can be one of the compounds (1)-(21) disclosed herein. In one embodiment, compound having the Formula (II) can be one of the compounds (22)-(30) disclosed herein. In one embodiment, the compound can be one of compounds (1), (2), or (4) disclosed herein.

The present invention also provides a pharmaceutical composition comprising a pharmaceutically acceptable carrier and a compound having (i) the Formula (I),

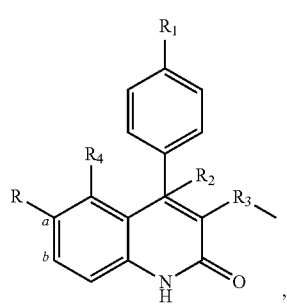

or a pharmaceutically acceptable salt thereof, wherein R is H,

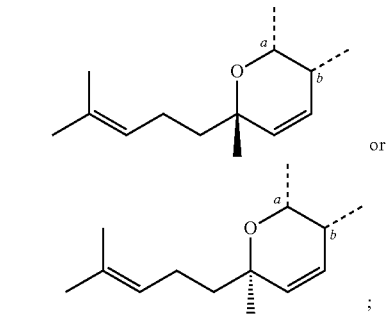

or R is formed together with the carbon atoms a and b of the phenyl group to which they are attached in the following substituent $R_1$ is H or OCH$_3$; $R_2$ is H, OH, or OCH$_3$; $R_3$ is H, OH, or OCH$_3$; and $R_4$ is H or OH; or (ii) the Formula (II),

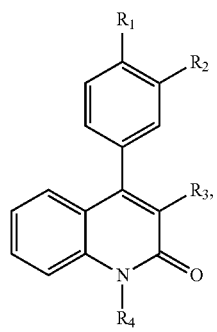

or a pharmaceutically acceptable salt thereof, wherein $R_1$ is H or $OCH_3$; $R_2$ is H or OH; $R_3$ is OH or $OCH_3$; and $R_4$ is H or $CH_3$.

In one embodiment, compound having the Formula (I) can be one of the compounds (1)-(21) disclosed herein. In one embodiment, compound having the Formula (II) can be one of the compounds (22)-(30) disclosed herein. In one embodiment, there is provided a method of using such composition to treat viral infection, for example, infection by HSV-1. In another embodiment, there is provided a method of using such composition to inhibit activities of HSV-1.

The term "pharmaceutically acceptable carrier or excipient" as used herein refers to any material or substance with which the active principle, i.e. a compound of this invention may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid.

EXAMPLES

Example 1

The following example illustrates the invention further. It is to be understood that the embodiments of the present disclosure are not to be limited to the following described exemplary embodiments, but is to be controlled by the limitations set forth in the claims and any equivalents thereof.

Antiviral Activity Against HSV-1

The antiviral activities against HSV-1 were evaluated by cytopathic (CPE) assay. Hep-2 monolayer cells were treated with trypsin enzyme and transferred to 96-well plates. HSV-1 viruses were seeded with Hep-2 cells in 96-well plates, with 2% RPMI-1640 medium, and incubated under 37° C., 5% $CO_2$. After more than 90% lesions, the virus-infected cells were repeatedly freezed and thawed for 3 times, centrifuged, and stored in the refrigerator at −80° C. Each tested compound was dissolved in 10 μL DMSO to make a homogeneous solution and the solution was diluted 10 times by one-to-one dilution with 2% RPMI-1640 medium. The solution gradient was added to the infected cells incubated in 96-well plates. Ribavirin was used as positive control. Normal cells alone and infected cells alone were used as control. All samples were incubated under 37° C., 5% $CO_2$. Examine pathological changes once every hour, for 24 h. After 90% lesion was observed in positive control, the supernatant was removed from the wells, and 1% neutral red was added. OD value was determined at 540 nm. $IC_{50}$ values of the tested compounds were calculated by Reed-Muench methods.

The result indicated that the quinolinone derivatives disclosed herein showed different inhibitory activity against HSV-1 virus with $IC_{50}$ values ranging from 0.05~100 μM.

TABLE 1

Anti-HSV-1 activity of tested compounds

| Compounds | $IC_{50}$/μM | TI = $TC_{50}/IC_{50}$ |
|---|---|---|
| 1 | A | ++++ |
| 2a | A | +++ |
| 3 | A | +++ |
| 4 | A | +++ |
| 5 | B | ++ |
| 6 | B | ++ |
| 7 | B | ++ |
| 10 | A | ++ |
| 11 | B | ++ |
| 12 | B | ++ |
| 15 | D | + |
| 16 | D | + |
| 17 | C | ++ |
| 18 | C | ++ |
| 19 | C | ++ |
| 22 | C | + |
| 23 | B | + |
| 24 | C | + |
| 27 | B | + |
| 28 | B | + |
| 29 | C | + |
| 30 | C | + |
| Ribavirin | D | ++++ |

"A" represents $IC_{50}$ was between 0.05 and 2 μM, "B" represents $IC_{50}$ was between 2 and 25 μM, "C" represents $IC_{50}$ was between 25 and 50 μM, "D" represents $IC_{50}$ was between 50 and 100 μM; "++++" means TI > 500, "+++" means TI was between 100 and 500, "++" means TI was between 20 and 100, "+" means TI < 20. $TC_{50}$ represents median toxic concentration for Hep-2 monolayer cells.

In summary, provided herein are quinolinone derivatives that can be obtained by large scale fermentation of natural microorganisms. These compounds and the pharmaceutical compositions thereof would be useful as anti-viral agents. In one embodiment, these compounds have potent anti-HSV-1 activities.

REFERENCES

[1] Chang-Lun Shao, Ru-Fang Xu, Chang-Yun Wang, Pei-Yuan Qian, Kai-Ling Wang, Mei-Yan Wei, Potent Antifouling Marine Dihydroquinolin-2(1H)-one-Containing Alkaloids from the Gorgonian Coral-Derived Fungus *Scopulariopsis* sp. Mar Biotechnol. 2015, 17:408-415.

[2] Min Chen, Chang-Lun Shao, Hong Meng, Zhi-Gang She, Chang-Yun Wang, Anti-Respiratory Syncytial Virus Prenylated Dihydroquinolone Derivatives from the Gorgonian-Derived Fungus *Aspergillus* sp. XS-20090B15. J. Nat. Prod. 2014, 77:2720-2724.

[3] Scott A. Ne, Sang Un Lee, Yukihiro Asami, Jong Seog Ahn, Hyuncheol Oh, Jonas Baltrusaitis, James B. Gloer, Donald T. Wicklow, Aflaquinolones A-G: Secondary Metabolites from Marine and Fungicolous Isolates of *Aspergillus* spp. J. Nat. Prod. 2012, 75:464-472.

[4] Kirstin Scherlach, Christian Hertweck, Discovery of aspoquinolones A-D, prenylated quinoline-2-one alkaloids from *Aspergillus nidulans*, motivated by genome mining, Org. Biomol. Chem. 2006, 4:3517-3520.

[5] Ryuji Uchida, Rie Imasato, Hiroshi Tomoda, Satoshi Ōmura, Yaequinolones, New Insecticidal Antibiotics Produced by *Penicillium sp.* FKI-2140', J. Antibiot. 2006, 59(10):646-658.
[6] Ryuji Uchida, Rie Imasato, Kazuro Shiomi, Hiroshi Tomoda, Satoshi Ohmura, Yaequinolones J1 and J2, Novel Insecticidal Antibiotics from *Penicillium* sp. FKI-2140. Org. Lett. 2005, 7(25):5701-5704.
[7] Yasuo Kimura, Miyako Kusano, Hiroyuki Koshino, Jun Uzawa, Shozo Fujioka, Kiyotsugu Tani, Penigequinolones A and B, Pollen-growth Inhibitors Produced by *Penicillium* sp., No. 410. Tetrahedron Letters. 1996, 37(28): 4961-4964.
[8] Thomas O. Larsen, Jrn Smedsgaard, Jens C. Frisvad, Uffe Anthoni, Carsten Christophersen, Consistent production of penigequinolone A and B by *Penicillium scabrosum*. Biochemical Systematics and Ecology. 1999, 27:329-332.
[9] Li-Ying Ma, Wei-Zhong Liu, Li Shen, Yu-Ling Huang, Xian-Guo Rong, Yan-Yan Xu, Xue-Dong Gao, Spiroketals, isocoumarin and indoleformic acid derivatives from saline soil derived fungus *Penicillium raistrickii*. Tetrahedron. 2012, 68:2276-2282.
[10] Hideo Hayashi, Tadashi Nakatani, Yoshiki Inoue, Mitsuru Nakayama, Hiroshi Nozaki, New Dihydroquinolinone Toxic to *Anemia salina* Produced by *Penicillium* sp. NTC-47. Biosci. Biotech. Biochem. 1997, 61(5):914-916.
[11] Miyako Kusano, Hiroyuki Koshino, Jun Uzawa, Shozo Fujioka, Tsuyoshi Kawano, Yasuo Kimura, Nematicidal Alkaloids and Related Compounds Produced by the Fugus *Penicillium* cf. *simplicissimum*. Biosci. Biotech. Biochem. 2000, 64(12):2559-2568.
[12] Yi Zhang, Jun Mu, Frank Essmannh, Yan Feng, Markus Kramer, Hai-yan Bao, Stephanie Grond, A new quinolinone and its natural/artificial derivatives from a shark gill-derived fungus *Penicillium crustosum* AP2T1. Natural Product Research. 2015.
[13] Cunningham K G., Freeman G G., Isolation and some chemical properties of viridicatin, a metabolic product of *Penicillium viridicatum*. Biochemical Journal. 1953, 53:328-332.
[14] Alex Ciegler, Ching T. Hou, Isolation of Viridicatin from *Penicillium palitans*. Arch. Mikrobiol. 1970, 73:261-267.

What is claimed is:

1. A method of inhibiting activities of herpes simplex virus 1 (HSV-1), comprising the step of contacting a cell with a compound having the formula

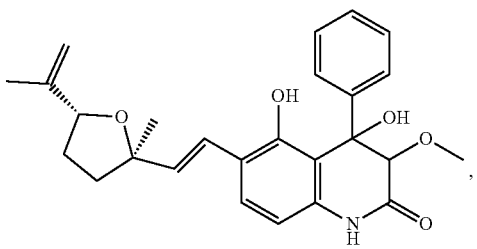 [SMILES: C=C(C)[C@H]1CC[C@](C)(/C=C/c2ccc3c(c2O)C(O)(c2ccccc2)C(OC)C(=O)N3)O1]

or a pharmaceutically acceptable salt thereof.

2. The method of claim 1, wherein the compound has the formula

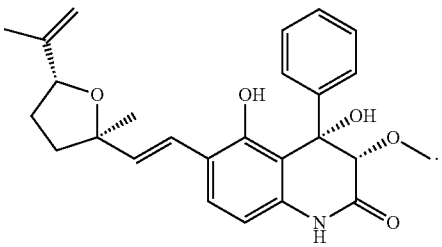 [SMILES: C=C(C)[C@H]1CC[C@](C)(/C=C/c2ccc3c(c2O)[C@@](O)(c2ccccc2)[C@H](OC)C(=O)N3)O1]

\* \* \* \* \*